United States Patent [19]

Shinoki et al.

[11] Patent Number: 5,447,846
[45] Date of Patent: Sep. 5, 1995

[54] HOMOGENEOUS IMMUNOASSAY PROCESS USING COVALENT CONJUGATE OF ENZYME AND PLURAL MONOCLONAL ANTIBODIES FOR DIFFERENT EPITOPES ON ANALYTE

[75] Inventors: Hiroshi Shinoki; Masashi Ogawa, both of Asaka, Japan

[73] Assignee: Fuji Photo Film C., Ltd., Kanagawa, Japan

[21] Appl. No.: 91,661

[22] Filed: Jul. 14, 1993

[30] Foreign Application Priority Data

Jul. 17, 1992 [JP] Japan .................................. 4-212394

[51] Int. Cl.⁶ .......................................... G01N 33/53
[52] U.S. Cl. .............................. 435/7.920; 435/7.930; 435/7.940; 435/7.950; 435/174; 435/14; 435/18; 435/22; 435/964; 435/969; 435/970; 435/972; 436/537; 436/538; 530/388.1; 530/391.1; 530/866
[58] Field of Search .................... 422/56, 60; 424/94.3, 424/85.8; 435/7.9, 7.92-7.95, 14, 18, 22, 174, 805, 962, 964, 969, 970, 972; 436/536, 537, 538, 541, 534, 548, 810, 819, 815; 530/350, 387.1, 388.1, 391.1, 866

[56] References Cited

U.S. PATENT DOCUMENTS

| | | | |
|---|---|---|---|
| 4,144,306 | 3/1979 | Figueras | 422/56 |
| 4,459,358 | 7/1984 | Berke | 422/56 X |
| 4,556,642 | 12/1985 | Collet-Cassart et al. | 436/500 |
| 4,636,479 | 1/1987 | Martin et al. | 436/533 |
| 4,690,890 | 9/1987 | Loor et al. | 435/7.9 |
| 4,692,404 | 9/1987 | Ashihara et al. | 435/22 X |
| 4,757,001 | 7/1988 | Ashihara et al. | 435/7.32 X |
| 4,804,626 | 2/1989 | Bellet et al. | 435/7.9 X |
| 4,968,742 | 11/1990 | Lewis et al. | 525/54.1 |
| 5,026,653 | 6/1991 | Lee et al. | 436/518 |
| 5,047,324 | 9/1991 | Frederickson | 435/7.9 |
| 5,168,057 | 12/1992 | Oh et al. | 435/174 |

FOREIGN PATENT DOCUMENTS

| | | |
|---|---|---|
| 0045103 | 3/1982 | European Pat. Off. .............. 436/533 |
| 0088974 | 9/1983 | European Pat. Off. . |
| 0095089 | 11/1983 | European Pat. Off. . |
| 0096463 | 12/1983 | European Pat. Off. . |
| 0407904 | 1/1991 | European Pat. Off. . |
| 0451848 | 10/1991 | European Pat. Off. . |
| 9007714 | 12/1990 | WIPO ................................... 435/7.9 |

OTHER PUBLICATIONS

S. Fernando et al, "Studies of the low dose 'hook'effect in a competitive homogenouse immunoassay," *J. of Immunol. Methods,* vol. 151 (1991) pp. 27-46.

T. Ngo, *"Enzyme-Mediated Immunoassays"* (Plenum Press New York 1985) pp. 3-19.

*Primary Examiner*—Carol A. Spiegel
*Attorney, Agent, or Firm*—McAulay Fisher Nissen Goldberg & Kiel

[57] ABSTRACT

An enzyme-labelled antibody adapted for use in a homogeneous immunoassay is provided. The enzyme-labelled antibody is a conjugate of an enzyme with two or more different monoclonal antibodies, each of the monoclonal antibodies being capable of specifically recognizing and binding to a different epitope of the same antigen. By using the enzyme-labelled antibody in the homogeneous enzyme immunoassay process, an analyte can be quantitatively analyzed at a higher sensitivity through a simple operation. Also provided is a dry immunoassay element comprising an immunological reaction layer containing the enzyme-labelled antibody. By the provision of such an immunoassay element, a further simplified quick analysis of an analyte is realized to give an accurate result.

24 Claims, 4 Drawing Sheets

HOMOGENEOUS IMMUNOASSAY PROCESS USING COVALENT CONJUGATE OF ENZYME AND PLURAL MONOCLONAL ANTIBODIES FOR DIFFERENT EPITOPES ON ANALYTE

BACKGROUND OF THE INVENTION

1. Field of the Invention

The present invention relates to an immunoassay for quantitatively determining a constituent present in a very small amount in a sample, in which a reaction between an antigen and an antibody is utilized. More particularly, the present invention relates to a homogeneous immunoassay process for quantitatively determining an analyte antigen (ligand) in the sample by the use of an enzyme-labelled antibody, an enzyme-labelled antibody used therein, and a dry immunoassay element in which the homogeneous immunoassay of the invention is applied.

Analyses of the constituents originated from the living body or chemicals contained in the body fluids, such as blood or urine, are useful for diagnosing the condition of diseases or judging the course of curing, and thus they occupy important parts in the field of clinical test. The so-called enzyme immunoassay has been known in the art as one method for analyzing such constituents (ligands) generally present in a small amount in the body fluids. The enzyme immunoassay may be classified into a heterogeneous system for which B/F (Bound/Free) separation must be effected, and a homogeneous system in which B/F (Bound/Free) separation is not necessary. Meantime, B stands for the labelling material in a complex formed by binding of the specific antibody (or specific antigen) to the ligand, and F stands for the free labelling material which is not bound to the ligand.

In the heterogeneous system, the antigen-antibody bound (B) formed by the reaction between the antigen and the antibody is separated from free antibody and antigen (F) by any suitable means and then the activity of the labelling enzyme in the antigen-antibody bound is determined. Although it is expected that the heterogeneous system has a high sensitivity in principle since the bound (B) is separated from free antibody and antigen (F), there is a problem that cumbersome operations are needed for the B/F separation and thus a relatively long time is necessary for the determination.

On the other hand, the reactions in the homogeneous system are based on the phenomenon that the enzymatic activity of the labelling enzyme is affected by some interference caused by binding of an antibody to the antigen (ligand), and the inhibition due to antigen-antibody binding is generally utilized. In general, the antigen is labelled with an enzyme so that the suppression in enzymatic activity either by a steric hindrance imposed on binding of the enzyme, which is bound to a generally large molecule antibody, with the substrate or by a change in three-dimensional structure of the enzyme is detected. For example, EMIT (Enzyme Multiplied Immunoassay Technique) is well-known as such a system.

Alternatively, when the antigen is a high molecular weight substance, the antibody may be labelled with an enzyme and the suppression in enzymatic activity due to the antigen-antibody binding reaction may be utilized. The operations in the homogeneous systems are relatively simplified since complicated B/F separation is not necessary. However, the homogeneous system has a disadvantage that the sensitivity thereof is relatively low in principle.

2. Prior Art Statement

An improved homogeneous immunoassaying process has been disclosed in Unexamined Japanese Patent Publication No. 108756/1985 (corresponding to U.S. Pat. No. 4,692,404 and EP 0144176A). In this prior-proposed process, a water-insoluble high molecular weight polymer substrate is used as the substrate for the enzyme. The enzymatic reaction takes place on the surfaces of the substrate particles, in other words, at the solid-liquid interface. As the result, the suppression in enzymatic activity due to steric hindrance caused by binding between the enzyme-labelled antibody and the antigen is exaggerated. However, improvement in sensitivity by this prior-proposed process is limited, and there is a demand for a more sensitive immunoassay process.

In the routine clinical tests in which a number of test samples are to be handled, it is demanded that the individual samples should be analyzed rapidly by simple operations, more desirously by automated operation sequence. To comply with the demand, dry analysis elements have been proposed (for example, by Unexamined Japanese Patent Publication Nos. 53888/1974 (corresponding to U.S. Pat. No. 3,992,158), 77356/1984 (corresponding to EP 0097952A) and 102388/1984 (corresponding to U.S. Pat. No. 4,861,552) and U.S. Pat. No. 4,459,358. It is desirous that the immunoassay process can be applied to such a dry analysis element.

OBJECTS AND SUMMARY OF THE INVENTION

Accordingly, a first object of the invention is to provide a homogeneous immunoassay process by which a highly sensitive analysis is ensured while using a simple operation.

A second object of the invention is to provide an enzyme-labelled antibody used in the homogeneous immunoassaying process of the invention.

A third object of the invention is to provide a dry enzyme immunoassay element for enabling a rapid analysis of a ligand while utilizing the homogeneous immunoassaying process of the invention.

The first object of the invention is attained by the provision of a homogeneous enzyme immunoassay process for quantitatively analyzing an antigen by determining the change in enzymatic activity caused by a reaction between said antigen and an enzyme-labelled antibody, characterized in that said enzyme-labelled antibody comprises two or more different monoclonal antibodies, each of the monoclonal antibodies being capable of specifically recognizing and binding to different epitopes of the same antigen.

The second object of the invention is attained by the provision of an enzyme-labelled antibody adapted for use in a homogeneous immunoassay, characterized in that said enzyme-labelled antibody is a conjugate of an enzyme with two or more different monoclonal antibodies, each of the monoclonal antibodies being capable of specifically recognizing and binding to different epitopes of the same antigen.

The third object of the invention is attained by the provision of a dry immunoassay element for quantitatively analyzing an antigen by determining the change in enzymatic activity caused by the reaction between said antigen and an enzyme-labelled antibody, comprising an immunological reaction layer containing an enzyme-labelled antibody essentially consisting of an enzyme and two or more monoclonal antibodies, each of the monoclonal antibodies being capable of specifically recognizing and binding to different epitopes of the same antigen.

The present invention is based on the finding that homogeneous enzyme immunoassay can be performed at an extremely high sensitivity by using an enzyme-labelled antibody which is prepared by binding one molecule enzyme with more than two sorts of monoclonal antibodies each recognizing and binding to an epitope (antigenic determinant) of an analyte antigen, the epitope being different from the other epitope of the same antigen, in place of a conventional enzyme-labelled antibody prepared by binding one molecule enzyme with one sort of monoclonal antibody. Although, it has not been clarified why the sensitivity is improved by the use of two or more different monoclonal antibodies, it is estimated that the sensitivity is improved for the following reason.

When the enzyme-labelled antibody reacts with an analyte antigen, the enzyme active site of the labelling enzyme generally suffers steric hindrance by the antigen, whereby the enzymatic activity is suppressed. The enzyme-labelled antibody used in the present invention is prepared by binding one molecule enzyme with two or more different antibodies each recognizing a different epitope (antigenic determinant) of the same analyte antigen. Accordingly, in the present invention, in addition to the formation of an antigen-antibody complex, an apparently polyvalent antigens reacts with a heterogeneous polyvalent antibodies (which form a bound product of two or more antibodies coupled together through one enzyme molecule) to form a matrix structure by bridging through antigen molecules and the enzyme molecule. The active site of the enzyme is covered by the thus formed matrix structure, leading to intense steric hindrance to the enzymatic activity due to the antigen-antibody binding reaction.

In a preferred embodiment of the invention, Fab', F(ab')$_2$ and Fab fragments may be used as the monoclonal antibodies. These fragments are preferred because they have no Fc portion which might cause noise. Fab' fragment is particularly preferred since it has SH group at the hinge region of the antibody to facilitate binding with the used enzyme.

When the immunoassaying process of the invention is applied for the preparation of a dry analysis element, the enzyme-labelled antibodies together with a substrate for the labelling enzyme may be contained in the same immunological reaction layer. This is because any enzymatic reaction does not take place when the dry analysis element is kept in dry condition unless it is used for immunoassay. The enzymatic activity of the enzyme is inhibited by the matrix structure of the antigens and the enzyme-labelled antibodies formed by the antigen-antibody reaction. Alternatively, only the enzyme-labelled antibodies may be contained in the immunological reaction layer and a separate substrate layer containing the substrate for the enzyme is provided. In the embodiment having a separate substrate layer, the matrix structure formed in the immunological reaction layer by the antigen-antibody reaction is trapped by the layer structure not to be transferred to the subsequent substrate layer. In any case, the amount of the analyte antigen in the sample can be detected by the suppression in enzymatic reaction.

DESCRIPTION OF PREFERRED EMBODIMENTS

Analyte (Substance to Be Analyzed)

Figure 1:
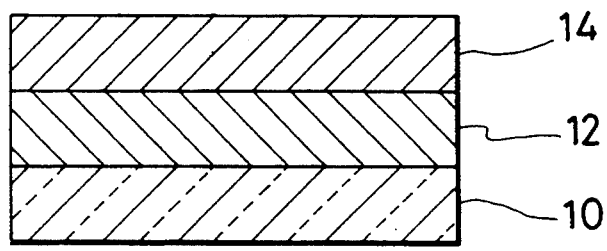
FIG. 1 is an illustration showing the layer structure of one embodiment of the immunoassay element according to this invention.

The substance to be analyzd by the present invention (hereinafter referred simply as "analyte") is a ligand having an antigenic determinant and contained in the sample. The sample containing the analyte is not limited and many kinds of sample may be analyzed by this invention, the typical examples including blood (whole blood, blood plasma, blood serum), lymph fluid and urine. It suffices that the ligand is an antigen having two or more different epitopes (antigenic determinants). However, it is not necessary that structural features of these epitopes are made clear or identified. It suffices that at least two sorts of monoclonal antibodies, which are immunologically discriminatable from each other, can be obtained. Examples of such antigens include plasma proteins such as albumin, immunoglobulin, ferritin and C-reactive proteins (CRP); viruses such as HB antigens; (hepatitis B virus antigen); bacteria; and α-getoprotein or like antigens contained in various tissues, blood or urine.

Antibody

Two or more monoclonal antibodies capable of recognizing and binding to different epitopes of the analyte antigen is used as the antibodies. The monoclonal antibodies are selected so as to be specific to at least two distinct binding site (i.e. epitope) of the analyte antigen molecule.

Monoclonal antibodies may be obtained and prepared by the conventional method. In detail, the antigen is injected into the peritoneal cavity of immuno-recipient animal (mouse) together with an adjuvant for several times. The spleen cells taken out from the recipient are fused with the murine myeloma cell using polyethylene glycol. The fused cells are subjected to cloning to obtain antibody producing cells which are proliferated as the monoclonal cells. The thus proliferated cells are injected intra-peritoneally to a mouse so as to obtain the ascites and the serum containing the monoclonal antibodies. The antibodies may be easily purified by the process in which ammonium sulfate precipitation, ion exchange chromatography, affinity chromatography (Protein-A agarose etc.) and gel filtration are combined.

The antibodies may be classified into sub-classes including IgG1, IgG2a and IgG2b, and the antibodies of IgG1 are particularly preferred since they are excellent in fragmenting efficiency at the step of preparing an enzyme-antibody complex. IgG1 may be digested by protease such as activated papain or pepsin, whereby the Fc region may be removed from intact IgG1 to prepare F(ab')2 fragment. The prepared F(ab')2 may be cleaved into Fab' fragment by the reduction of S—S linkage.

In a preferred embodiment of the invention, Fab' fragments are used as the monoclonal antibodies. An intact antibody (IgG) has the Fab (antigen-binding region) and the Fc (complement fixing region). When an intact antibody is bound to an enzyme to be used as the enzyme-labelled antibody in the analysis of a blood sample, the complement constituents contained in the blood sample tend to bind the Fc region to cause steric hindrance thereby to inhibit the enzymatic activity. Although the sample is not blood, non-specific adsorption is resulted by the presence of Fc region, leading to the result that the antibodies are adsorbed to the wall of the used reaction vessel or the pores and surfaces of internal cavities of the porous material used for constructing the immunological reaction layer, whereby the apparent activity of the enzyme-labelled antibody is lowered to cause noise in the determination step. It is thus desirous to use Fab', F(ab')2 or Fab fragments containing no Fc region as the antibodies in order to exclude such noise. The most preferable antibody is a Fab' fragment containing a free SH group which is readily combined with an enzyme.

Selection of the monoclonal antibodies for the determination of different epitopes may be effected through the ELISA (enzyme-linked immunosorbent assay). For example, an antigen is bound to a micro-titer plate coated or sensitized with a monoclonal antibody 1, and then another biotinized monoclonal antibody 2, which is separately prepared, is allowed to react with the the antigen. Additional binding of the biotinized monoclonal antibody 2 with the antigen is examined by using avidin-POD (peroxidase). When the reaction is positive, it is judged that the antibody 1 and the antibody 2 recognize and bind to different epitopes. Thus, a combination of two monoclonal antibodies are respectively specific to two distinct epitope of the macromolecule (i.e. antigen) under investigation.

Labelling Enzyme

The enzyme for forming the enzyme-antibody conjugate may be selected in consideration of the combination of the substrate which is used at the subsequent enzymatic reaction. Since the reactivity to the enzyme which reacts with the substrate is suppressed by the steric hindrance by the presence of the matrix structure formed by the enzyme, the antigen and the antibody according to the present invention, it is preferable that the combination of the enzyme and the substrate is selected so that the influence by the steric hindrance is easily detected. It is thus preferred to attain a higher sensitivity that a substrate having a relatively large molecular weight is selected. A substrate having a molecular weight of not less than about 20,000 daltons, preferably not less than about 100,000 daltons is used in the invention. Examples of such substrates include starch as the substrate for enzyme amylase; substrate cellulose as the substrate for enzyme cellulase; proteins such as gelatin and hemocyanin as the substrate to protease and various oils and fats as the substrate for lipase. Detailed reports relating to the selection of the enzymes and substrates are disclosed in Unexamined Japanese Patent Publication Nos. 108756/1985 (corresponding to EP 0144176A and U.S. Pat. No. 4,692,404), 171461/1985 (corresponding to EP 0152305A and U.S. Pat. No. 4,757,001) and 171460/1985 (corresponding to EP 0152305A and U.S. Pat. No. 4,757,001). Amylase used with starch as the substrate is preferred. It is particularly preferred that the substrate is a water-insoulble substrate, since the steric hindrace by the presence of the enzyme-antibody-antigen matrix structure is noticeably appeared.

Usable amylases include α-amylase, β-amylase and glucoamylase, and it is preferable for the prevention of noise to use an amylase which is not substantially contained in the sample. These amylases are contained in various resources including animals (saliva, pancreatic juice, etc.), plants and bacteria. When a body fluid or blood of human being or an animal is analysed, it is preferable that the use of an amylase originated from a higher animal is obviated.

Examples of amylase originated from bacteria or plants include glucoamylases originated from Aspergillus, Rhizopus or Saccharomyces; α-amylases originated from malt of barley, wheat and soybean; α-amylases originated from *Bacillus Subtilis, Streptomyces griseus, Pseudomonas stutzeri* and *Thermoactiomyces vulgaris*. The most preferable amylase is the α-amylase originated from *Bacillus Subtilis*, because it is excellent in liquefying power and resistance to heat.

It is preferable that the enzyme is not affected by any hindering factor present in the sample, and that competitive homologous enzymes are not present in the sample. However, if an enzyme homologous to the labelling enzyme is present in the sample, an enzyme inhibitor may be used. It suffices that the used enzyme inhibitor inhibits activity of the enzyme contained in the sample to a greater extent than the inhibiting activity of the labelling enzyme. Most preferably, the used enzyme inhibitor inactivates the enzyme in the sample completely and does not deactivate the labelling enzyme. However, in practice, it suffices that the blank value at the measuring step is not raised by the use of the enzyme inhibitor, the restoration of the activity of the enzyme contained in the sample after the measuring step, which might caused by deactivation of the used enzyme inhibitor, being allowable. It is allowable that the enzyme inhibitor inhibits the activity of free enzyme as far as it does not inhibit the enzyme in the enzyme-labelled antibody. An enzyme inhibitor having the specific characteristics as described above may be selected from known enzyme inhibitors and used in the invention. Alternatively, an antibody which is contained in a sample to cause a problem is prepared and the thus prepared antibody is used as an enzyme inhibitor.

When an α-amylase is used as the enzyme, carboxymethylated starch, starch, amylose, amylopectin or like may be used as the substrate. It is particularly preferred for the improvement in sensitivity to use water-insoluble starch, since the enzymatic reaction takes place on the surfaces of the substrate particles, namely the reaction takes place at the solid-liquid interface to exaggerate the influence of steric hindrance to the enzymatic activity by the occurrence of antigen-antibody binding. Alternatively, a water-insoluble dye-starch may be used, followed by detection of the dye bound to the soluble amylose which is the decomposition product of enzymatic reaction. An example of commercially available water-insoluble blue starch polymer is Neoamylase (produced by Daiich Pure Chemicals, Co., Ltd.).

Linking between Enzyme and Monoclonal Antibody

The enzyme may be linked to the monoclonal antibody while utilizing the functional groups (amino, carboxyl, thiol, etc.) of the enzyme and the monoclonal antibody. Representative linking methods include the glutaraldehyde method, the periodic acid method, the pyridyl-disulfide method, and the maleimide-succinimide method. The linking method is not limited only to the reperesentative methods as described above, and may be selected from the methods described in "Method in Immunology and Immunochemistray", vol. 1, (C. A. Williams, M. W. Chase, Academic Press (1967)) or "KOSO MEN'EKI SOKUTEI-HO (Enzyme Immunoassay), edited by Ishikawa, Kawai and Miyai, Igaku Shoin, 1978. The maleimide-succinimide method, in which thiol group at the hinge region of the antibody is linked with amino group of the enzyme, is preferred since it is excellent in reaction efficiency while retaining the activity of the antibody.

In the maleimide-succinimide method, the enzyme is linked with two different Fab', for example, through the following steps. Initially, amino groups of the enzyme are maleimidated by the maleimide-succinimide reagent. The reaction product is subjected to gel filtration for purification, and then subjected to the reaction for forming a conjugate with two different monoconal antibodies (Fab') specifically recognizing different epitopes. It is preferable that the molar ratio of enzyme to antibodies in the conjugate forming reaction ranges from 1:3 to 1:7. For example, when a Fab' (having a molecular weight of about 50,000) is used as the antibody and an $\alpha$-amylase (having a molecular weight of about 50,000) is used as the the enzyme, the preferable weight ratio of the $\alpha$-amylase to the total weight of the Fab's ranges, from $\frac{1}{3}$ to 1/7. This linking reaction proceeds generally at 4° C. to room temperature.

The thus prepared enzyme-antibody complex (enzyme-labelled antibody) is purified through gel filtration, and dried through lyophilization as desired. The ratio between the enzyme and each monoclonal antibody in the linked product is not limited to 1:1, but may be changed to a desired ratio in consideration of the applied use of the product. In general, since the enzyme has plural amino groups, plural maleimide groups are introduced and linked with plural antibody molecules. Since at least one antibody molecule having a certain epitope and at least one antibody having a different epitope shall be introduced to one enzyme molecule, the molar ratio of antibodies to the enzyme in the produced complex must range more than 2:1 and preferably ranges from 4 to 5 in order to ensure high detection sensitivity. When Fab' fragments (each having a molecular weight of about 50,000) is used as the antibodies and an $\alpha$amylase (having a molecular weight of about 50,000) is used as the enzyme, the preferable molecular weight of the enzyme-antibody complex ranges from 150,000 daltons, more preferable from 250,000 to 300,000 daltons, to ensure high detection sensitivity.

Assaying Process (Wet Process)

The analyte antigen contained in the sample is allowed to contact with the enzyme-antibody complex in a solution. It is preferred that the temperature of the solution ranges from about 20° C. to 45° C., and the pH value of the solution ranges from about 4.0 to about 8.5. Buffer solutions such as a phosphate buffer or acetate buffer solution may be used to maintain the pH value of the solution at the constant level. The time for allowing the antigen to contact with the enzyme-antibody complex may be determined to ensure complete reaction, for example, ranging from 20 to 30 minutes when the temperature of the solution is 37° C. Then, a substrate for the labelling enzyme is added to the solution, and the enzymatic activity of the enzyme-antibody complex is measured. The presence of analyte antigen is detected as the suppression in enzymatic activity. By preparing a calibration curve drawn by using solutions each containing a known quantity of the analyte antigen, the analyte antigen contained in the sample can be quantitatively analyzed.

In an alternative embodiment, only the reaction between the antigen and the enzyme-antibody complex is performed in a solution system, and the reaction mixture after the reaction may be analyzed by using a dry system. In detail, a dry analysis element having a substrate layer containing the substrate for the labelling enzyme is prepared, and the reaction mixture after the completion of, the immuno-reaction between the antigen and the enzyme-antibody complex is spotted on the dry analysis element to measure the enzymatic activity. Such a dry analysis element has the layer structure similar as that of each dry analysis element described below except that the immunological reaction layer is excluded.

Layer Structure of Dry Immunoassay Element

The dry immunoassay element, in which the immunoassaying process of the invention is applied, will now be described. FIG. 1 shows an embodiment of the dry immunoassay element according to the invention.

Referring to FIG. 1, reference numeral 10 designates a transparent support on which a detection layer (or reagent layer) 12 and an immunological reaction layer 14 are laminated.

The immunological reaction layer 14 is composed of a water-permeable material and contains the enzyme-labelled antibody according to the invention and a non-diffusible substrate which is a substrate for the labelling enzyme.

The reagent layer 12 is composed of a water-permeable layer and contains a reagent composition for detecting the product (diffusible material) of the enzymatic reaction, the product of the enzymatic reaction being diffused and transferred from the immunological reaction layer 14. When the product of enzymatic reaction is a material which may be directly detected, such as a colored product, the layer 12 needs not contain any detection reagent composition and thus the layer 12 serves as the detection layer.

The analyte (antigen) contained in the liquid sample spotted on the analysis element forms a matrix structure in the immunological reaction layer 14 as the result of conjugate-forming reaction between the enzyme-labelled antibody and the antigen. The enzymatic activity to the substrate contained in the immunological reaction layer 14 is thus suppressed. Accordingly, the quantity of antigen contained in the sample is determined by measuring the quantity of the product of enzymatic reaction detected in the reaction layer (or detection layer) 12.

Figure 2:
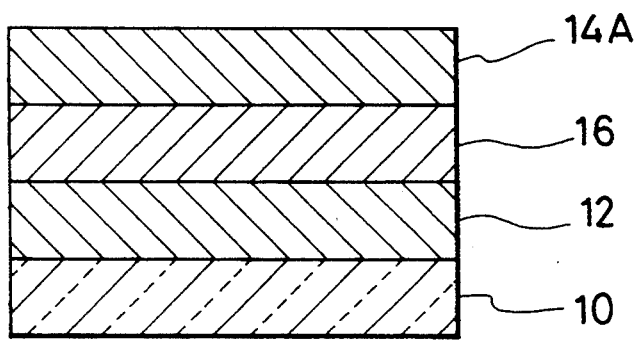
FIG. 2 is an illustration showing the layer structure of another embodiment of the immunoassay element according to this invention.

The enzyme-labelled antibody and the substrate for the labelling enzyme may be contained in separate layers. In such an embodiment, a substrate layer 16 composed of water-permeable material and containing the substrate for the labelling enzyme is laminated on the reagent layer (or detection layer) 12, and an immunological reaction layer 14A containing the enzyme-labelled antibody is laminated on the layer 16. In such an embodiment, the analyte (antigen) contained in the liquid sample spotted on the dry analysis element proceeds an antigen-antibody binding reaction with the enzyme-labelled antibody in the immunological reaction layer 14A to form a matrix structure which is substantially immobile. The enzyme-labelled antibody which has not been bound to the antigen (together with the matrix structure which is small enough not to be trapped by the material forming the layer 14A) is transferred to the substrate layer 16. In both of the embodiments of FIGS. 1 and 2, the enzyme immunological reaction proceeds in the dry analysis element by only spotting the liquid sample on the analysis element.

The dry immunoassay element according to the invention has the principal layer structure as described above. An additional layer may be introduced to prepare a dry analysis element having the layer structure similar to that of a variety of the known dry analysis elements. In detail, in addition to the immunological reaction layer (or the immunological reaction layer and the substrate layer) and the reagent layer (or the detection layer), the analysis element of the invention may have a multi-layered structure including a support layer, spreading layer, detection layer, light-shielding layer, adhesive layer, water-absorbing layer, undercoating layer or other desired layers. The construction of multi-layer structure has been disclosed, for example in Unexamined Japanese Patent Publication No. 53888/1974 (corresponding to U.S. Pat. No. 3,992,158), Unexamined Japanese Patent Publication No. 40191/1976 (corresponding to U.S. Pat. No. 4,042,335), Unexamined Japanese Patent Publication No. 164356/1980 (corresponding to U.S. Pat. No. 4,292,272), Unexamined Japanese Patent Publication No. 4959/1986 (corresponding to EP-0166365A).

When a light-transmitting and water-impermeable support is used, the dry immunoassay element having the following construction may be used, although the present invention is not limited to the following constructions.

(1) a support, a reagent layer, and an immunological reaction layer superposed in this order;
(2) a support, a reagent layer, a substrate layer, and an immunological reaction layer superposed in this order;
(3) a support, a reagent layer, an adhesive layer, and an immunological reaction layer superposed in this order;
(4) a support, a reagent layer, an adhesive layer, a substrate layer, and an immunological; reaction layer superposed in this order;
(5) a support, a detection layer, a reagent layer, and an immunological reaction layer superposed in this order;
(6) a support, a reagent layer, a substrate layer, and an immunological reaction layer superposed in this order;
(7) a support, a reagent layer, a light-reflecting layer, and an immunological reaction layer superposed in this order;
(8) a support, a reagent layer, a light-reflecting layer, a substrate layer and an immunological reaction layer superposed in this order;
(9) a support, a detection layer, a reagent layer, a light-reflecting layer, and an immunological reaction layer superposed in this order;
(10) a support, a detection layer, a reagent layer, a light-reflecting layer, a substrate layer and an immunological reaction layer superposed in this order;
(11) a support, a detection layer, a light-reflecting layer, a reagent layer and an immunological reaction layer superposed in this order;
(12) a support, a detection layer, a light-reflecting layer, a reagent layer, a substrate layer, and an immunological reaction layer superposed in this order;
(13) a support, a second reagent layer, a light, reflecting layer, a first reagent layer, and an immunological reaction layer superposed in this order;
(14) a support, a second reagent layer, a light-reflecting layer, a first reagent layer, a substrate layer and an immunological reaction layer superposed in this order;
(15) a support, a detection layer, a second reagent layer, a light-reflecting layer, a first reagent layer, and an immunological reaction layer superposed in this order; and
(16) a support, a detection layer, a second reagent layer, a light-reflecting layer, a first reagent layer, a substrate layer and an immunological reaction layer superposed in this order.

In the constructions set forth in (1) to (12), the reagent layer may comprise plural separate layers. A water-absorbing layer may be interposed between the support and the reagent or detection layer. A filtering layer may be interposed between adjacent layers. A spreading layer may be provided on the substrate layer. Alternatively, the substrate layer may have spreading function to serve as the spreading layer. A suitable filtering layer may be provided on the top of the analysis element when a solid constituents, such as blood cells, are contained in the sample.

Immunological Reaction Layer and Substrate Layer

Each of the immunological reaction layers 14, 14A and the substrate layer is composed on a water-permeable layer. In order to ensure water-permeability of these layers, it is preferable that each of these layers is a porous layer composed of a porous medium or a layer made of a hydrophilic polymer binder.

The porous layer may be fibrous or non-fibrous. As the fibrous material, filter paper, non-woven cloth, woven cloth (e.g. plain woven cloth), knitted cloth (e.g. tricot knitted cloth) or filter paper made of glass fibers may be used. Examples of the non-fibrous material may be either one of a membrane filter composed of cellulose acetate described in Unexamined Japanese Patent Publication No. 53888/1974 (corresponding to U.S. Pat. No. 3,992,158), or a particulate structure layer containing interconnected voids and composed of inorganic or organic fine particles as disclosed in Unexamined Japanese Patent Publication Nos. 3888/1974 (corresponding to U.S. Pat. No. 3,992,158), 90859/1980 (corresponding to U.S. Pat. No. 4,258,001) and 70163/1983 (correponding to U.S. Pat. No. 4,486,537). A laminated structure made of partially bonded multiple porous layers may also be preferably used, examples of such structure being disclosed in Unexamined Japanese Patent Publication Nos. 4959/1986 (corresponding to EP 0166365A), 116258/1987, 138756/1987 (corresponding to EP 0226465A), 138757/1987 (corresponding to EP 0226465A) and 138758/1987 (corresponding to EP 0226465A).

The porous layer may be a spreading layer having a so-called metering function to spread a liquid over an area substantially in proportion to the volume of the liquid fed thereto. Preferable materials for the spreading layer are woven and knitted fabrics. The woven fabrics or like may be subjected to the glow discharge treatment as described in Unexamined Japanese Patent publication No. 66359/1982 (corresponding to U.S. Pat. No. 4,783,315 and GB 2,087,974A). In order to adjust the area or rate for spreading, the spreading layer may contain a hydrophilic polymer or a surfactant as described in Unexamined Japanese Patent publication Nos. 222770/1985 (corresponding to EP 0162301A), 219397/1988 (corresponding to U.S. Pat. No. 4,889,797, U.S. Pat. No. 4,916,059 and EP 0207406A), 112999/1988 (corresponding to U.S. Pat. No. 4,889,797, U.S. Pat. No. 4,916,059 and EP 0207406A) and 182652/1987 (corresponding to DE 37 17 913A).

One convenient method for impregnating the substrate in the porous layer is a method wherein the substrate is impregnated into or coated on a porous membrane made of, for example, paper, cloth or a high polymer, and then the composite is applied on another water-permeable layer, for example, a reagent layer superposed on the support by a method as described in Unexamined Japanese Patent publication No. 164356/1980 (corresponding to U.S. Pat. No. 4,292,272). A further method comprises the steps of bonding a porous layer on another water-permeable layer (for example, a reagent layer) by a method as described above, and coating a composition containing the substrate on the porous layer. Any known methods may be employed for the impregnation or coating on the porous layer. Coating may be effected by selecting a suitable method, for example, dip coating, doctor coating, hopper coating and curtain coating.

Although the thickness of the substrate layer made by any of the aforementioned methods is not limited, the thickness may range within 1 $\mu$m to 50 $\mu$m, and preferably, from 2 $\mu$m to 30 $\mu$m, when the layer is provided as a coating layer. When it is provided by another method, for example by piling of a laminate, the thickness thereof may be varied within a wide range of from several tens of $\mu$m to several hundreds of $\mu$m.

The immunological reaction layer 14, 14A or the substrate layer 16 may be a water-permeable layer composed of a hydrophilic polymer binder, such as gelatin and derivatives thereof (e.g. phthalated gelatin), derivatives of cellulose (e.g. hydroxyethyl cellulose), agarose, sodium alginate, acrylamide copolymers, methacrylamide copolymers, copolymers of acryl amides or methacrylamides with various vinyl monomers, polyhydroxyethyl methacrylate, polyvinyl alcohol, polyvinyl pyrrolidone, sodium polyacrylate, and copolymers of acrylic acid with various vinyl monomers.

The substrate layer composed of a hydrophilic polymer binder may be provided by coating an aqueous solution or dispersion of the substrate, an additional other reagent composition and a hydrophilic polymer binder on another layer, such as a support or a detection layer, and then drying the coated solution or dispersion, as disclosed in the specifications of Japanese Patent Publication No. 21677/1988 (corresponding to U.S. Pat. No. 3,992,158), Unexamined Japanese Patent publication Nos. 164356/1980 (corresponding to U.S. Pat. No. 4,292,272), 101398/1979 (corresponding to U.S. Pat. No. 4,132,528), and 292063/1986 (Chemical Abstracts, 106, 210567y). The thickness of the dried substrate layer containing a hydrophilic polymer as the binder may range from about 2 $\mu$m to about 50 $\mu$m, and preferably, from about 4 $\mu$m to about 30 $\mu$m, and the coverage thereof may range from about 2 g/m$^2$ to about 50 g/m$^2$, and preferably from about 4 g/m$^2$ to about 30 g/m$^2$.

To improve the characteristics, such as, coating characteristics, diffusibility of the diffusible material, reactivity and storage stability, the substrate layer may include, in addition to the non-diffusible substrate, various organic or inorganic additives, for example, enzyme activators, coenzymes, surfactants, pH buffer reagents, fine particles, antioxidants, etc. Examples of buffer system, which may be contained in the substrate layer, include pH buffer reagents as described in "KAGAKU BINRAN, KISOHEN" edited by Japanese Chemical Society (MARUZEN, Tokyo, 1966), pp1312–13,20; R. M. C. Dawson et al., "Data for Biological Research", 2nd Edition (Oxford at the Clarendon Press, 1969), pp476–508; "Biochemistry", 5, pp467–477 (1966); and "Analytical Biochemistry", 104, pp300–310 (1980). Specific examples of usable buffers are buffer reagents containing tris(hydroxymethyl)aminomethane (Tris), buffer reagents containing phosphates, buffer solutions containing borates, buffer reagents containing citric acid or citrates, buffer reagents containing glycine, buffer solutions containing Bicine, and buffer reagents containing HEPES.

The immunological reaction layer may have the construction similar to the substrate layer described above. Meanwhile, when it is desired to contain the substrate and the enzyme-labelled antibody in one or two adjacent layers substantially in the dry state or substantially in the absence of water, the enzyme-labelled antibody may be dissolved or dispersed in a non-aqueous solvent such as an alcohol (e.g. ethanol) and then the solution or dispersion is impregnated in a water-permeable layer.

Reagent Layer and Detection Layer

The reagent layer 12 contains a reagent composition for detecting the diffusible material which has diffused and migrated from the immunological reaction layer 14 (or the substrate layer 16). If necessary, a fragmenting enzyme may be contained in the reagent composition and a detection reagent composition for detecting the lower molecular weight product formed by the action of the fragmenting enzyme may also be contained. The reagent layer is composed of a water-permeable layer which is preferably a continuous layer made of a hydrophilic polymer binder, similar to the water-permeable layers as described in the description of the substrate layer. The used hydrophilic polymer binder may be determined in consideration of the diffusible product formed in the substrate layer and the coloring reagent contained in the reagent layer.

When the diffusible material diffused and migrated from the immunological reaction layer 14 (or the substrate layer 16) is a material which can be directly detected, the layer 12 needs not contain any detection reagent composition so that the layer 12 serves as a detection layer. When the layer 12 is a detection layer, it is desirous that the layer 12 is composed of a continuous layer composed of a hydrophilic polymer binder selected from the water-permeable layers as described hereinbefore in the description relating to the substrate layer.

Support

The support 10 may be light-nontransmitting (opaque), light-semi-transmitting (translucent) or light-transmitting (transparent), and it is generally preferable that the support is light-trasmitting and water-impermeable. Preferable materials for the light-transmitting and water-impermeable support are polyethylene terephthalate and polystyrene. In general, an undercoating is provided or the support is subjected to hydrophilization treatment in order to firmly adhere the hydrophilic layer.

Labelling Enzyme/Non-Diffusible substrate/Fragmenting Enzyme

In the dry immunoassay element of the invention, the sensitivity can be improved by adding a fragmenting enzyme for further fragmenting the diffusible material, which is the decomposed product of the non-diffusible substrate by the labelling enzyme, to a lower molecular weight material to the reagent layer 12, in the same manner as described in Unexamined Japanese Patent Publication Nos. 295446/1991 (corresponding to EP-0451848A), 128655/1992 (corresponding to U.S. Ser. No. 07/763,198) and 276551/1992 (corresponding to EP 0503459A). The combination of the labelling enzyme and the fragmenting enzyme may be selected so that the labelling enzyme reacts with the non-diffusible substrate to form a diffusible material which is further fragmented by the fragmenting enzyme to form a lower molecular weight product which can be easily detected.

In detail, the labelling enzyme of the enzymeslabelled antibody is selected so that it decomposes the non-diffusible polymer substrate to form a diffusible product which can be further fragmented by the fragmenting enzyme to form a lower molecular weight product. The non-diffusible substrate is selected so that the substrate per se is non-diffusible (insoluble)in the aqueous sample liquid and thus does not diffuse or migrate from the immunological reaction layer 14 (or the substrate layer 16) to the ragent layer 12. The fragmenting enzyme is selected so that it fragments the diffusible substance or material produced from the non-diffusible substrate under the action of the labelling enzyme to produce a lower molecular weight product which is easily detected. Specific examples of the labelling enzyme, non-diffusible substrate and fragmenting enzyme will be described below.

Labelling Enzyme

Examples of suitable enzyme include hydrolase which form diffusible oligomers from non-diffusible substrates composed of polymers. Among the labelling enzymes described hereinbefore, glucosidase is preferred. Examples of glucosidase are α-amylase, β-amylase, glucoamylase and lysozyme.

Non-Diffusible Substrate

Examples of the substrate for said α-amylase, β-amylase and glucoamylase are calboxymethylated starch and starch. When calboxymethylated starch or starch is used as the non-diffusible substrate, α-amylase may be used as the labelling enzyme, and glucoamylase or α-glucosidase may be combined as the fragmenting enzyme as will be described hereinafter.

Fragmenting Enzyme

The fragmenting enzyme may be an enzyme of the same kind as of the labelling enzyme. In such a case, it is preferred that the labelling enzyme is an endo-active enzyme which fragments or digests the molecule intramolecularly to produce an oligomer, and that the fragmenting enzyme has an exo-activity to act the molecule at the terminal thereof to produce a monomer. For instance, when the non-diffusible substrate is a plymer (e.g. starch), a fragmenting enzyme for decomposing the diffusible oligomer (e.g. maltose) produced by the action of the labelling enzyme to a monomer, (e.g. glucose) is used. Examples of the fragmenting enzyme include hydrolases for saccharides, specific example being α-amylase, β-amylase, glucoamylase and α-glucosidase. When carboxymethyl cellulose if used as the non-diffusible substrate and cellulase is used as the labelling enzyme, CI enzyme may be used as the fragmenting enzyme.

The combination of the labelling enzyme, the non-diffusible substrate and the fragmenting enzyme may be selected from the enzymes and substrates described in the known publications (for example, "Enzyme Handbook" (Bunji Maruo and Nobuo Tamiya, Asakura Shoten, 1982); and "Biochemical Handbook" (Nobumasa Imura et al., Maruzen, 1984)

The lower molecular weight product produced by fragmentation in the reagent layer by the action of the fragmenting enzyme may be optically detected by using a known detection reagent. Any known methods may be employed for detecting the final glucose which is formed by the action of the aforementioned fragmenting enzyme, the examples being a method in which hydrogen peroxide formed by the oxidation of glucose in the presence of glucose oxidase is detected (e.g. the method wherein a Trinder reagent is used, as described in Ann. Clin. Biochem., 6 24 (1964) and J. Clin. Pathol., 22, 246 (1969), the method wherein a Trinder reagent is used, as described in Unexamined Japanese Patent Publication No. 50991/1974 (corresponding to U.S. Pat. No. 3,886,045), U.S. Pat. No. 3,992,158 and Unexamined Japanese Patent Publication No. 164356/1980 (corresponding to U.S. Pat. No. 4,292,272), the method wherein a reagent containing a triaryl-substituted imidazole leuco dye is used, as described in Unexamined Japanese Patent Publication No. 26188/1978 (corresponding to U.S. Pat. No. 4,089,747) and Unexamined Japanese Patent Publication No. 45557/1983 (Chemical Abstracts, 99, (1983): 209284j), the method wherein a reagent containing an imidazole leuco dye substituted with a diarylmonoaralkyl, as described in Unexamined Japanese Patent Publication Nos. 193352/1984 (corresponding to EP 0122641A) and 224677/1985 (corresponding to U.S. Pat. No. 4,665,023), a method wherein NADH produced in the presence of glucose dehydrogenase and NAD is detected, and a method wherein glucose-6-phosphate produced in the presence of hexokinase is detected. Amongst these detection methods, the most preferred is the method wherein glucose is oxidized in the presence of glucose oxidase to form hydrogen peroxide which is detected using peroxidase and a leuco dye because of its high detection sensitivity.

These detection reagent may be contained in the reagent layer 12 of the analysis element together with the fragmenting enzyme, or may be contained in another layer (for example, a second reagent layer or a detection layer) disposed below the reagent layer 12 to detect the produced lower molecular weight product. When a leuco dye if used, it is preferred that the dye is dispersed in the hydrophilic binder in a solution in a water-immiscible solvent in consideration of the stability of the formed dye.

Process for Preparing the Immunoassay Element

The dry immunoassay element of the invention may be prepared by any of the known processes described in the specifications of the aforequoted patents.

The analysis element of the invention may be cut into a square piece having sides each ranging from about 15 to about 30 mm or a disk having a substantially same area. It is preferred, in view of the preparation, packaging, shipping, storage and measuring operations, that the element be contained in a slide frame as described, for example, in Japanese Patent Publication No. 28331/1982 (corresponding to U.S. Pat. No. 4,169,751), Unexamined Japanese Utility Model Publication No. 142354/1981 (corresponding to U.S. Pat. No. 4,387,990), Unexamined Japanese Patent publication No. 63452/1982, Unexamined Japanese Utility Model Publication No. 32350/1983 and Unexamined Japanese Patent Publication No. 501144/1983 (corresponding to International Publication W.O. 83/00391) for use as a slide for chemical analysis. For the convenience in some uses, it may be formed in a long tape shape which is contained in a cassette or magazine, or a small piece thereof may be applied on or contained in a card having an opening.

Analyzing Method Using the Immunoassay Element

The analysis element of the invention may be used for the quantitative analysis of an analyste ligand in a sample liquid by using it through the operations described in the specifications of the aforequoted patents.

For example, about 5 μl to about 30 μl, preferably μ8 1 to 15 μl, of an aqueous sample liquid, such as, serum, plasma or urine, is spotted or otherwise fed on the substrate layer 14. The analysis element spotted with the sample liquid is then incubated at a constant temperature of from about 20° C. to about 45° C., preferably at a constant temperature of from about 30° C. to about 40° C., for 1 to 10 minutes. The reflection optical density of the color or the change in color in the element may be measured from the light-transmitting support side, and the quantity of the ligand contained in the sample can be determined using a preliminarily prepared calibration curve based on the principle of colorimetry. The volume of the spotted liquid sample and the time and temperature for incubation are maintained constant to improve the accuracy in quantitative analysis.

The measuring operation may be carried out while using the chemical analysis apparatus described in Unexamined Japanese Patent Publication Nos. 125543/1985, 220862/1985 and 294367/1986 to realize a quantitative analysis at a high accuracy by extermely easy operations.

Meantime, a semi-quantitative analysis may be conducted by judging the degree of coloring by naked eye if such visual judgment is adequate for the object or required accuracy.

When the analysis element does not contain the enzyme-labelled antibody, the aqueous sample liquid is mixed with a solution containing the enzyme-labelled antibody to complete the binding reaction, and then spotted on the substrate layer.

(Synthesis Example 1)

Preparation of GMB Amylase:

Maleimide groups were introduced into α-amylase through the following processing steps. To 1 ml of a 10 mg/ml solution of Bacillus subtilis α-amylase solution (in a 0.1M glycerophosphate buffer solution, pH 7.0), 100 μl of a 100 mg/ml solution of GMBS (N-(γ-maleimido-butyryloxy)succinimide; produced by DOJIN KAGAKU) was added and allowed to react at room temperature for 2 hours. The reaction mixture was subjected to the gel filtration through a SEPHADEX G-25 column, and the passing fraction was collected to obtain (N-(γ-maleimido-butyryloxy)amidated amylase (GMB amylase). The concentration of the thus obtained GMB amylase solution was 1.12 mg/ml.

(Synthesis Example 2)

Preparation of Anti-human CRP IgG Fab' (First Antibody: Fab'-α):

Each of two different monoclonal antibodies IgG against the human CRP was prepared through a commonly used process in which immunized cells (spleen cells) obtained by immunizing to mouse were fused with murine myeloma cells, followed by cloning process. The Fab' fragment for each of two different monoclonal antibodies (first and second antibodies) was prepared, after confirming that each monoclonal antibody specifically recognizes different epitope of the same antigen.

4.4 mg of the first anti-human CRP antibody IgG was dissolved in 1 ml of a 0.1M acetate buffer solution (pH 5.5) and then added with 132 μg of activated papain, followed by stirring the mixture at 37° C. for 2 hours. The reaction mixture was then applied to a SUPERDEX-200 gel column, which had been preliminarily equilibrated with a 0.1M phosphate buffer solution (pH 6.0, containing 1 mM EDTA-2Na), followed by elution with the same phosphate buffer solution. The peak fraction of the eluate having the molecular weight of about 100,000 daltons was collected to obtain an anti-human CRP IgG F(ab')$_2$. 5 ml of a 0.1M phosphate buffer solution (pH 6.0) containing 2.2 mg of the thus prepared anti-human CRP IgG F(ab')$_2$ was added with 100 μl of a 113 mg/ml aqueous solution of 2-mercaptoethylamine-HCl salt to proceed the reaction at 37° C. for 2 hours with stirring. The reaction mixture was subjected to gel filtration by a SEPHADEX-25, which had been preliminarily equilibrated with a 0.1M glycerophosphate buffer solution (pH 7.0, containing 5 mM EDTA-Ca), to collect the passing fraction. The thus prepared anti-human CRP IgG Fab' (hereinafter referred to as "Fab'-α") fraction was diluted with the same buffer solution to the concentration of the solution to 0.1 mg/ml.

(Synthesis Example 3)

Preparation of Anti-human CRP IG Fab'$_2$ (Second antibody: Fab'-β):

5.3 mg of the second anti-human CRP antibody was dissolved in 1 ml of a 0.1M acetate buffer solution (pH 5.5) and then added with 159 μg of activated papain, followed by stirring the mixture at 37° C. for 2 hours. The reaction mixture was then applied to a SUPERDEX-200 gel column, which had been preliminarily equilibrated with a 0.1M phosphate buffer solution (pH 6.0, containing 1 mM EDTA-2Na), followed by elution with the same phosphate buffer solution. The peak fraction at the molecular weight of about 100,000 daltons was collected to obtain an anti-human CRP IgG F(ab')$_2$. 5 ml of a 0.1M phosphate buffer solution (pH 6.0) containing 3.1 mg of the thus prepared anti-human CRP IgG F(ab')$_2$ was added with 100 μl of a 113 mg/ml aqueous solution of 2-mercaptoethylamine-HCl salt to proceed the reaction at 37° C. for 2 hours with stirring. The reaction mixture was subjected to gel filtration by a SEPHADEX G-25, which had been preliminarily equilibrated with a 0.1M glycerophosphate buffer solution (pH 7.0, containing 5 mM EDTA-Ca), to collect the passing fraction. The thus prepared anti-human CRP IgG Fab' (hereinafter referred to as "Fab'-β")

fraction was diluted with the same buffer solution to the concentration of the solution to 0.1 mg/ml.

(Synthesis Example 4)

Preparation of α-Amylase/Fab'-α/Fab'-β Bound:

3.65 ml for each of two Fab' fragments (Fab'-α and Fab'-β) prepared by Synthesis Examples 2 and 3 were mixed together and added with 108 μl of the GBM amylase solution prepared by Synthesis Example 1, and the reaction admixture was maintained at 4° C. for 20 hours to proceed the reaction. The reaction admixture was then applied to a SUPERDEX-200, which had been preliminarily equilibrated with a 0.1M glycerophosphate buffer solution (pH 7.0, containing 0.5 mM EDTA-Ca), followed by elution with the same glycerophosphate buffer solution. The peak fraction of the eluate having the molecular weight of about 270,000 daltons was collected to obtain an aimed enzyme-labelled antibody (α-amylase/Fab'-α/Fab'-β bound ). The bound had a molecular weight of a molecule obtained by coupling one molecule of the enzyme with four molecule in total of Fab'-α and Fab'-β.

(Synthesis is Example 5)

Preparation of α-Amylase/Fab'α Bound (Comparative Example 1):

An enzyme-antibody bound (conjugate), in which the labelling enzyme was bound to only one monoclonal antibody, was prepared as a comparative example. 3.65 ml of a 0.1 mg/ml solution of anti-human CRP IgG Fab' (Fab'-α) prepared by Synthesis Example 2 was added with 54 μl of the GBM amylase solution prepared by Synthesis Example 1, and the reaction mixture was maintained at 4° C. for 20 hours to proceed the reaction. The reaction mixture was then applied to a SUPERDEX-200, which had been preliminarily equilibrated with a 0.1M glycerophosphate buffer solution (pH 7.0, containing 0.5 mM EDTA-Ca), to effect elution using the same glycerophosphate buffer solution. The peak fraction at the molecular weight of about 270,000 was collected to obtain an enzyme-labelled antibody (α-amylase/Fab'-α bound) of comparative Example 1. The bound had a molecular weight of a molecule obtained by coupling one molecule of the enzyme with four molecule of Fab'-α.

(Synthesis is Example 6)

Preparation of α-Amylase/Fab'-β Bound (Comparative Example 2):

An enzyme-antibody bound, in which the labelling enzyme was bound to another monoclonal antibody, was prepared as a comparative example. 3.65 ml of a 0.1 mg/ml solution of anti-human CRP IgG Fab' (Fab'-β) prepared by Synthesis Example 3 was added with 54 μl of the GBM amylase solution prepared by Synthesis Example 1, and the reaction mixture was maintained at 4° C. for 20 hours to proceed the reaction. The reaction mixture was then applied to a SUPERDEX-200, which had been preliminarily equilibrated with a 0.1 M glycerophosphate buffer solution (pH 7.0, containing 0.5 mM EDTA-Ca), to effect elution by using the same glycerophosphate buffer solution. The peak fraction of the eluate having the molecular weight of about 270,000 was collected to obtain an enzyme-labelled antibody (α-amylase/Fab'-β bound) of Comparative Example 2. The bound had a molecular weight of a molecule obtained by coupling one molecule of the enzyme with four molecule of Fab'-β.

(Example 1)

Determination of Human CRP (Wet Process):

Using the enzyme-labelled antibody prepared by Synthesis Example 4, human CRP was analyzed by a homogeneous immunoassay. A series of human CRP solutions having concentrations ranging from 0 to 3.7 μg/ml was prepared by diluting such that a first diluted solution had a concentration corresponding to ⅓ of 3.7 μg/ml, and a second diluted solution had a concentration corresponding to ⅓ of the first diluted solution and so on. 50 μl for each of the sequentially diluted solutions was reacted with the α-amylase/Fab'-α/Fab'-β bound at 37° C. for 20 minutes to obtain a series of reaction solutions. On the other hand, one tablet of Neo Amylase Test "Dai-ichi" (produced by Daiich Pure Chemicals Co., Ltd. containing 45 mg of blue starch and 3 mg of BSA) was dissolved in 4 ml of a 50 mM maleate buffer solution (pH 6.5) to prepare a test solution. 1 ml of the test solution was added to each of the reaction solutions to proceed enzymatic reaction at 37° C. for an hour, and then added with 5 ml of an aqueous 0.5N NaOH solution to stop reaction. After agitating, the solution was subjected to centrifugation at 3,000 rpm for 5 minutes, and the supernatant was taken out. The supernatant was subjected to light absorption analysis at 620 nm to determine the quantity of blue dye which had been solubilized by the enzymatic reaction and dissolved in the supernatant. Similarly, using the enzyme-labelled antibodies of Comparative Examples 1 and 2 prepared by Synthesis Examples 5 and 6, the same human CRP was analyzed.

Figure 3:
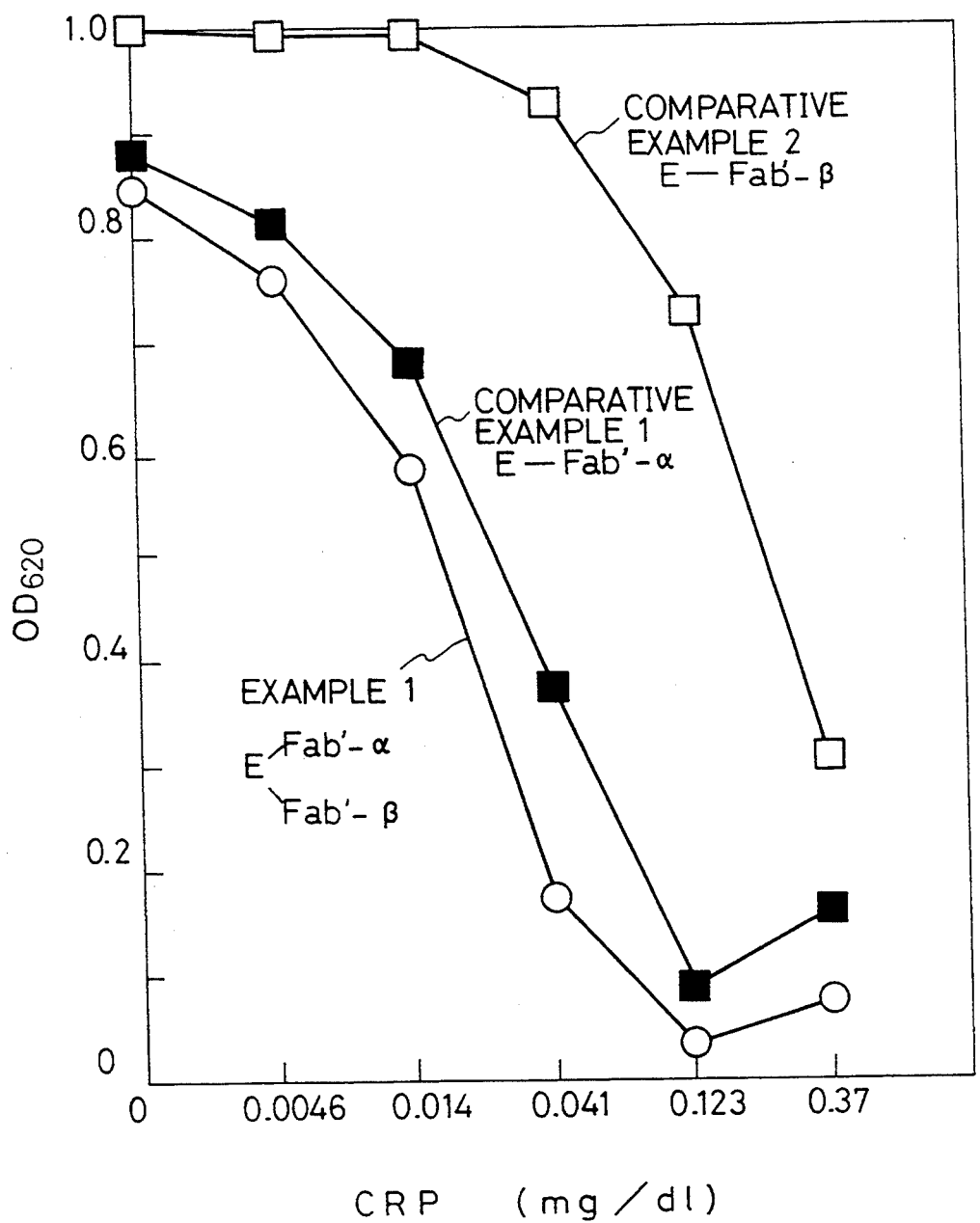
FIG. 3 is a graphic representation showing the calibration curves in the homogeneous immunoassay processes (wet processes) conducted by using the enzyme-labelled antibodies of Example 1 and Comparative Examples 1 and 2.

FIG. 3 shows the interrelation between the absorbancy and the concentration of human CRP. As shown in FIG. 3, the calibration curve of CRP in the Example 1 of the invention (shown by -○-) is shifted to the lower concentration side as compared with the calibration curves in the Comparative Examples 1 and 2 (shown by -■- and -□- ). This reveals that the Example of the invention prepared by binding one enzyme molecule (E) with two kinds of monoclonal antibodies (Fab'-α and Fab'-β) each binding to different epitope is more effectively used to give more sensitive detection than the Comparative Examples 1 and 2 each prepared by binding only one kind of monoclonal antibody to one eyzyme molecule.

(EXAMPLE 2)

On a colorless and transparent polyethylene terephthalate (PET) sheet (support) coated with a gelatin undercoating and having a thickness of 180 μm, coated was a reagent solution containing a cross-linking reagent, followed by drying, to form a reagent layer so that respective components had the coverages as set forth below.

| | |
|---|---|
| Alkaline-treated Gelatin | 14.5 g/m² |
| Nonylphenoxypolyethoxyethanol (Containing 9 to 10 (average) of Oxyethylene Unit) | 0.2 g/m² |
| Glucose Oxidase | 5,000 U/m² |
| Peroxidase | 15,000 U/m² |
| Glucoamylase | 5,000 U/m² |
| 2-(4-hydroxy-3,5-dimethoxyphenyl)-4-[4-(dimethylamino)phenyl]-5-phenetyl-imidazole (Leuco Dye) Acetate | 0.38 g/m² |
| Bis[(vinylsulfonylmethylcarbonyl)amino]-methane | 0.1 g/m² |

An adhesive layer was coated on the reagent layer to have the following coverage, and then dried.

| | |
|---|---|
| Alkaline-treated Gelatin | 14.5 g/m² |
| Bis[(vinylsulfonylmethylcarbonyl)amino]-methane | 0.1 g/m² |

Then, an aqueous solution containing the following reagent was coated over the surface of the adhesive layer to have the following coverages to swell the gelatin layer and a tricot knitted cloth made by knitting PET spun yarn of 36 gage corresponding to 50 deniers and having a thickness of about 250 μm was laminated thereon, by pressing with a uniform light pressure to form a porous spreading layer.

| | |
|---|---|
| Nonylphenoxypolyethoxyethanol (containing 9 to 10 (average) of Oxyethylene Units) | 0.15 g/m² |
| Bis[(vinylsulfonylmethylcarbonyl)amino]-methane | 0.4 g/m² |

Thereafter, a substrate layer was formed by coating a substrate, followed by drying, to have the following coverages, whereby a multi-layered analysis element for the quantitative analysis of CRP was prepared.

| | |
|---|---|
| Carboxymethylated Starch | 5 g/m² |
| Nonylphenoxypolyethoxyethanol (containing 9 to 10 (average) of Oxyethylene Units) | 0.2 g/m² |

The thus prepared element was cut into tips each having 15 mm square, and each tip was placed in a slide frame described in Unexamined Japanese Patent Publication No. 63452/1982 to prepare a multi-layered dry slide 1 for the analysis of CRP according to this Example.

Test for Appraisal of the Propertis:

The α-amylase/Fab'- α/Fab'-β bound prepared by Synthesis Example 4 was added to a 50 mM glycerophosphate buffer solution (pH 7) containing a predetermined quantity of CRP to prepare a solution containing the bound in a concentration of 0.1 mg/ml. The thus prepared solution was incubated at 37° C. for 20 minutes. 10 μl of the incubated solution was spotted on the aforementioned slide 1 which was maintained at 37° C., and the optical density of the reflected light having a wavelength of 650 nm was measured from the PET support side. The difference in optical density ($\Delta OD_{5-3}$) of the reflected lights measured respectively after the lapse of 3 minutes and 5 minutes was determined. A calibration curve was prepared based on the result of determination. Calibration curves were drawn through similar procedures by using the enzyme-labelled antibody (α-amylase/Fab'-α bound) of Comparative Example 1 prepared by Synthesis Example 5 and the enzyme-labelled antibody (α-amylase/Fab'-β bound) of Comparative Example 2 prepared by Synthesis Example 6.

Figure 4:
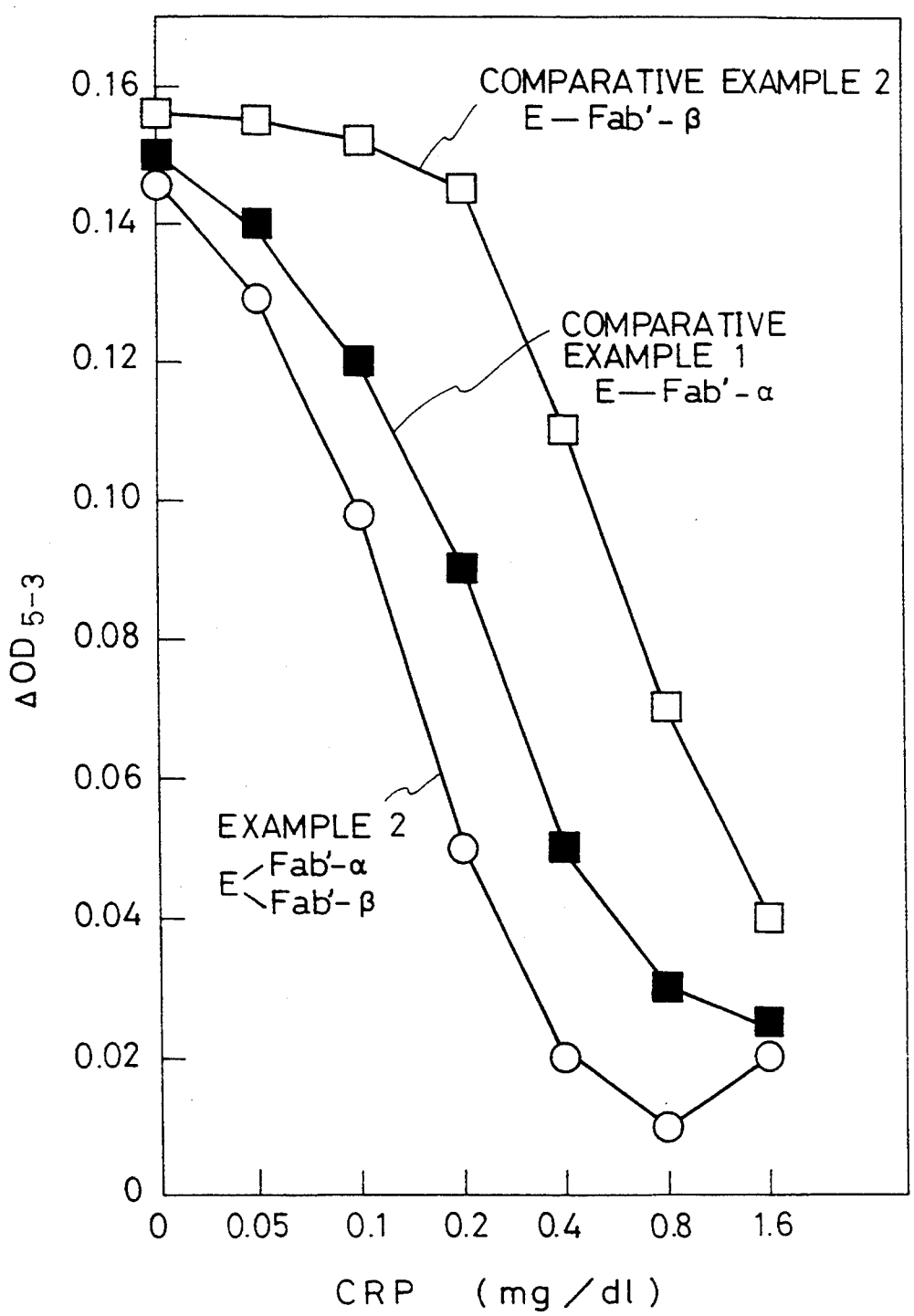
FIG. 4 is a graphic representation showing the calibration curve when the immunoassay element of Example 2 is used, the antigen-antibody reaction taking place in a solution and only the enzymatic reaction taking place in the analysis element.

The thus prepared calibration curves are shown in FIG. 4. As shown in FIG. 4, the calibration curve in the Example 2 of the invention (shown by -○-) is shifted to the lower concentration side as compared with the calibration curves in the Comparative Examples 1 (shown by -■-) and Comparative Example 2 (shown by -□-). This reveals that more sensitive detection can be realized by the present invention.

(EXAMPLE 3)

Similar to Example 2, a multi-layered analysis element having a tricot knitted cloth layer was prepared. On the tricot knitted cloth layer, which served both as a substrate layer and a spreading layer, coated was a solution of the enzyme-labelled antibody (α-amylase/-Fab'-α/Fab'-β bound) prepared by Synthesis Example 4 in ethanol to have a coverage of 3 mg/m², followed by drying, to prepare a multi-layered immunoassay slide 2 for the analysis of CRP.

Comparative slides 3 and 4 were prepared similar to the slide 2 by using, in place of the enzyme-labelled antibody of Synthesis Example 4, the α-amylase/Fab'-α bound prepared by Synthesis Example 5 and the α-amylase/Fab'-β bound prepared by Synthesis Example 6.

Figure 5:
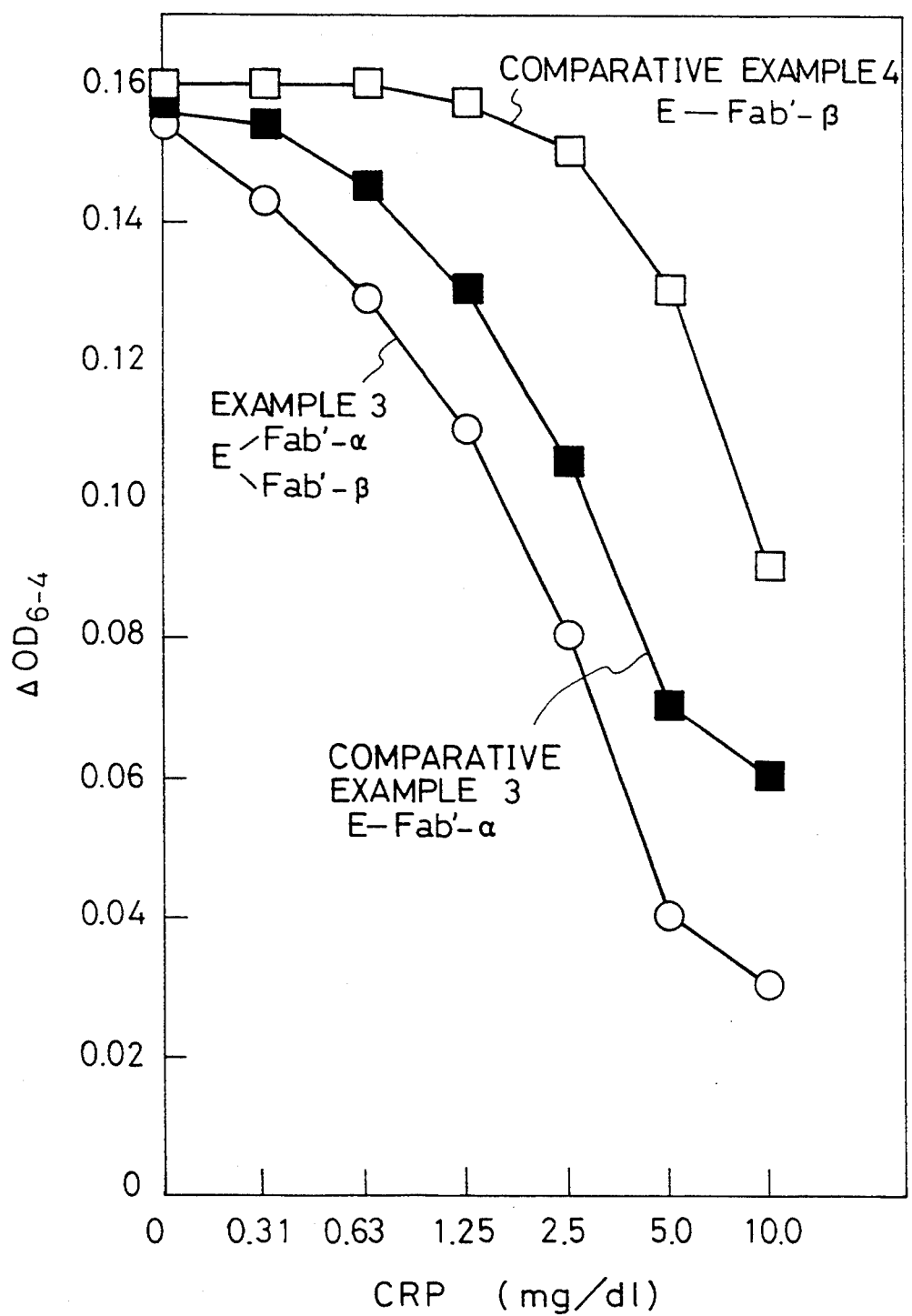
FIG. 5 is a graphic representation showing the calibration curve when the immunoassay element of Example 3 is used, both of the antigen-antibody reaction and the enzymatic reaction taking place in the analysis element.

Test for Appraisal of the Properties:

10 μl of a 50 mM glycerophosphate buffer solution containing a known quantity of CRP was spotted on each of the slides 2, 3 and 4. Each slide was maintained at 37° C., and the optical density of the reflected light having a wavelength of 650 nm was measured from the PET support side. Measurements were carried out to know the difference in optical density ($\Delta OD_{6-4}$) between the optical density of the reflected light measured after the lapse of 4 minutes from spotting and the optical density of the reflected light measured after the lapse of 6 minutes from spotting. Calibration curves were prepared from the results of measurements. As shown in FIG. 5, the calibration curve obtained by using the slide 2 (shown by -○-) of Example 3 is shifted to the lower contentration side than the calibration curves obtained by using the comparative slide 3 (shown by -■-) and the comparative slide 4 (shown by -□-). The results reveal that the sensitivity of the dry analysis element can be improved by the application of the immunoassaying process of the invention.

As has been described in detail hereinbefore, the enzyme-labelled antibody according to the present invention is prepared by coupling a labelling enzyme with two or more different monoclonal antibodies each recognizing and binding to different epitope of the antigen. By using the present enzyme-labelled antibody in a homogeneous immunoassay process, the sensitivity of immunoassay can be considerably improved. In addition, the present invention provides a homogeneous immunoassaying process in which cumbersome B/F separation is not needed to simplify the necessary operations. The immunoassaying process can also be applied to a dry analysis element to realize easier and faster analysis at high sensitivity.

What is claimed is:

1. A homogeneous enzyme immunoassay process for determining a polyvalent analyte antigen in an aqueous liquid sample by measuring inhibition of enzymatic activity caused by steric hindrance due to an antigen-antibody binding reaction, comprising:

(a) contacting the sample with an enzyme-antibody conjugate wherein said enzyme is covalently coupled to two or more different monoclonal antibodies or immunoreactive fragments thereof, each of the monoclonal antibodies or immunoreactive fragments thereof specifically recognizing and binding to a different and non-overlapping epitope of the same polyvalent analyte antigen, in order to form a matrix structure of said enzyme-antibody conjugate and said polyvalent analyte antigen, wherein the thus formed matrix structure inhibits the enzymatic activity of the enzyme;

(b) measuring the uninhibited enzymatic activity of the enzyme by reacting the enzyme with a specific substrate for the enzyme; and (c) determining the amount of said polyvalent analyte antigen in the sample from the uninhibited enzymatic activity measured in step (b).

2. The process according to claim 1, wherein said enzyme is covalently coupled to two or more Fab' fragments.

3. The process according to claim 1, wherein said enzyme is covalently coupled to two or more F(ab')$_2$ fragments.

4. The process according to claim 1, wherein said enzyme is covalently coupled to two or more Fab fragments.

5. The process according to claim 1, wherein said enzyme is an endo-active hydrolase and said specific substrate has a high molecular weight of not less than 20,000 daltons.

6. The process according to claim 1, wherein said enzyme is an endo-active hydrolase and said specific substrate is a water-insoluble substrate.

7. An enzyme-antibody conjugate for use in analyzing a polyvalent analyte antigen in an aqueous liquid sample by a homogeneous immunoassay process, wherein said enzyme is covalently coupled to two or more different monoclonal antibodies or immunoreactive fragments thereof, each of the monoclonal antibodies or immunoreactive fragmetns thereof specifically recognizing and binding to a different and non-overlapping epitope of the polyvalent analyte antigen, wherein said enzyme-antibody conjugate specifically binds the polyvalent analyte antigen to form a matrix structure of said enzyme-antibody conjugate and said polyvalent analyte antigen, wherein the thus formed matrix structure inhibits the enzymatic activity of the enzyme.

8. The enzyme-antibody conjugate according to claim 7, wherein said enzyme is covalently coupled to two or more Fab' fragments.

9. The enzyme-antibody conjugate according to claim 7, wherein said enzyme is covalently coupled to two or more F(ab')$_2$ fragments.

10. The enzyme-antibody conjugate according to claim 7, wherein said enzyme is covalently coupled to two or more Fab fragments.

11. A dry immunoassay element for determining a polyvalent analyte antigen in an aqueous liquid sample by measuring inhibition of enzymatic activity caused by steric hindrance due to an antigen-antibody binding reaction, comprising:

an immunological reaction layer containing an enzyme-antibody conjugate wherein the enzyme is covalently coupled to two or more different monoclonal antibodies or immunoreactive fragments thereof, each of the monoclonal antibodies or immunoreactive fragments thereof, specifically recognizing and binding to a different and non-overlapping epitope of the polyvalent analyte antigen, said enzyme-antibody conjugate being capable of forming a matrix structure of said enzyme-antibody conjugate and said polyvalent analyte antigen when the aqueous liquid sample is added to the immunological reaction layer, wherein the thus formed matrix structure inhibits the enzymatic activity of the enzyme.

12. The dry immunoassay element according to claim 11, wherein said enzyme is endo-active hydrolase, and wherein said immunological reactive layer contains a non-diffusible substrate which forms a diffusible material by the action of said enzyme free from the formed matrix structure.

13. The dry immunoassay element according to claim 12, further comprising a reagent layer laminated below said immunological reaction layer and containing an exo-active hydrolase for further fragmenting said diffusible material into a lower molecular weight product.

14. The dry immunoassay element according to claim 13, wherein said non-diffusible substrate is a polysaccharide having a molecular weight of not less than 20,000 daltons, the endo-active hydrolase is an endo-active glucosidase, and the exo-active hydrolase is an exo-active glucosidase.

15. The dry immunoassay element according to claim 14, wherein the lower molecular weight product is glucose.

16. The dry immunoassay element according to claim 13, wherein said reagent layer or another water-permeable layer contains a reagent composition which reacts with said lower molecular weight product to form a dye having an absorption peak in the visible wavelength range.

17. The dry immunoassay element according to claim 11, further comprising a substrate layer laminated below said immunological reaction layer and containing a non-diffusible substrate which forms a diffusible material by the action of said enzyme free from the formed matrix structure.

18. The dry immunoassay element according to claim 17, further comprising a reagent layer laminated below said immunological reaction layer and containing an exo-active hydrolase for further fragmenting said diffusible material into a lower molecular weight product.

19. The dry immunoassay element according to claim 18, wherein said non-diffusible substrate is a polysaccharide having a molecular weight of not less than about 20,000 daltons, the endo-active hydrolase is an endo-active glucosidase, and the exo-active hydrolase is an exo-active glucoside.

20. The dry immunoassay element according to claim 19, wherein the lower molecular weight product is glucose.

21. The dry immunoassay element according to claim 18, wherein said reagent layer or another water-permeable layer contains a reagent composition which reacts with said lower molecular weight product to form a dye having an absorption peak in the visible wavelength range.

22. The dry immunoassay element according to claim 11, wherein said enzyme is covalently coupled to two or more Fab' fragments.

23. The dry immunoassay element according to claim 11, wherein said enzyme is covalently coupled to two or more F(ab')$_2$ fragments.

24. The dry immunoassay element according to claim 11, wherein said enzyme is covalently coupled to two or more Fab fragments.

* * * * *